(12) United States Patent
Hood et al.

(10) Patent No.: US 6,687,120 B2
(45) Date of Patent: Feb. 3, 2004

(54) COMPUTER SYSTEM INCLUDING SPEAKER-ANTENNA ASSEMBLY

(75) Inventors: Chuck Hood, Ceder Park, TX (US); David William Grunow, Round Rock, TX (US)

(73) Assignee: Dell Products L.P., Round Rock, TX (US)

( * ) Notice: Subject to any disclaimer, the term of this patent is extended or adjusted under 35 U.S.C. 154(b) by 136 days.

(21) Appl. No.: 09/981,034

(22) Filed: Oct. 17, 2001

(65) Prior Publication Data

US 2003/0072131 A1 Apr. 17, 2003

(51) Int. Cl.⁷ .............................. G06F 1/16; H04B 1/34
(52) U.S. Cl. ..................... 361/683; 343/720; 455/569.1
(58) Field of Search ................................ 361/679–686; 343/720, 702; 455/416, 569.1

(56) References Cited

U.S. PATENT DOCUMENTS

| 3,720,874 A | | 3/1973 | Gorcik et al. ................. 325/16 |
|---|---|---|---|
| 3,863,157 A | | 1/1975 | Quinlan et al. ............. 325/365 |
| 5,263,875 A | * | 11/1993 | Spicer et al. ................ 361/686 |
| 5,295,089 A | * | 3/1994 | Ambasz ...................... 361/681 |
| 5,422,433 A | * | 6/1995 | Rivera et al. ............... 361/800 |
| 5,430,617 A | * | 7/1995 | Hsu ........................... 361/683 |
| 5,771,441 A | * | 6/1998 | Altstatt ........................ 343/720 |
| 6,081,207 A | * | 6/2000 | Batio .......................... 361/680 |
| 6,282,433 B1 | * | 8/2001 | Holshouser ................. 343/702 |
| 6,336,037 B1 | * | 1/2002 | Sekine et al. ............... 343/702 |
| 6,400,321 B1 | * | 6/2002 | Fenwick et al. ............. 343/702 |

* cited by examiner

Primary Examiner—Lisa Lea-Edmonds
(74) Attorney, Agent, or Firm—Haynes and Boone, LLP

(57) ABSTRACT

A computer system includes a speaker-antenna assembly in the base of the system. Multiple speaker-antenna assemblies are situated in spaced apart relationship in the base in one embodiment. This provides both audio separation and isolation between the antennas for space and frequency diversity operation. By locating the speaker and antenna in a common assembly, substantial space savings are achieved.

20 Claims, 8 Drawing Sheets

COMPUTER SYSTEM INCLUDING SPEAKER-ANTENNA ASSEMBLY

BACKGROUND

The disclosures herein relate generally to computer systems and more particularly to computer systems employing wireless technology.

Personal computer systems in general and Intel/Microsoft compatible personal computer systems in particular have attained widespread acceptance. These personal computer systems now provide computing power to many segments of today's modern society. A personal computer system can usually be defined as a desktop, floor-standing, or portable microcomputer that includes a system unit having a system processor with associated volatile and non-volatile memory, a display, a keyboard, and one or more mass storage devices such as a floppy diskette drive, a CD-ROM or DVD drive, for example. One of the distinguishing characteristics of these systems is that they generally use a system board or motherboard to electrically connect many of these components together. Personal computer systems are information handling systems which are designed primarily to provide independent computing power to a single user, (or a relatively small group of users in the case of personal computers which serve as server systems.) Today, notebook, sub-notebook and personal digital assistant (PDA) devices have joined and become a part of personal computer systems on the smaller end of the size spectrum.

As wireless technology proliferates it is becoming increasingly important to equip computer systems with efficient antennas. Outboard antennas are generally not desirable because they can be easily broken. Alternatively, an antenna can be placed in the display of computer systems wherein the display is pivotally attached to the base. However, that approach has the disadvantage of a long coaxial cable length needed between the base and the antenna in the display. Another drawback of that approach is the continuous flexure of the coaxial cable at the pivot point between the base and the display. This can lead to premature failure.

Therefore, what is needed is a computer system with an internal antenna which consumes a low amount of space in the computer interior without long cable runs. However, mounting an antenna on the interior of a portable computer is challenging because the antenna must compete for already very limited space. Moreover, the internal antenna should be located in a manner which does not unduly distort the antenna's radiation pattern. Another challenge to be overcome is to position the internal antenna in a manner avoiding radio frequency (RF) noise problems.

SUMMARY

Accordingly, one embodiment of the disclosed computer system includes a base having an input device and a processor situated therein. The computer system also includes a memory coupled to the processor to facilitate execution of computer programs by the processor. A display is mounted to the base. A first speaker-antenna assembly is situated in the base. In another embodiment, a second speaker-antenna assembly is situated in the base in spaced-apart relationship with respect to the first speaker-antenna assembly.

A principal advantage of this embodiment is that by integrating an antenna and a speaker in an antenna-speaker assembly inside the computer system, a very low amount of valuable interior computer real estate or space is consumed.

DETAILED DESCRIPTION

Figure 1:
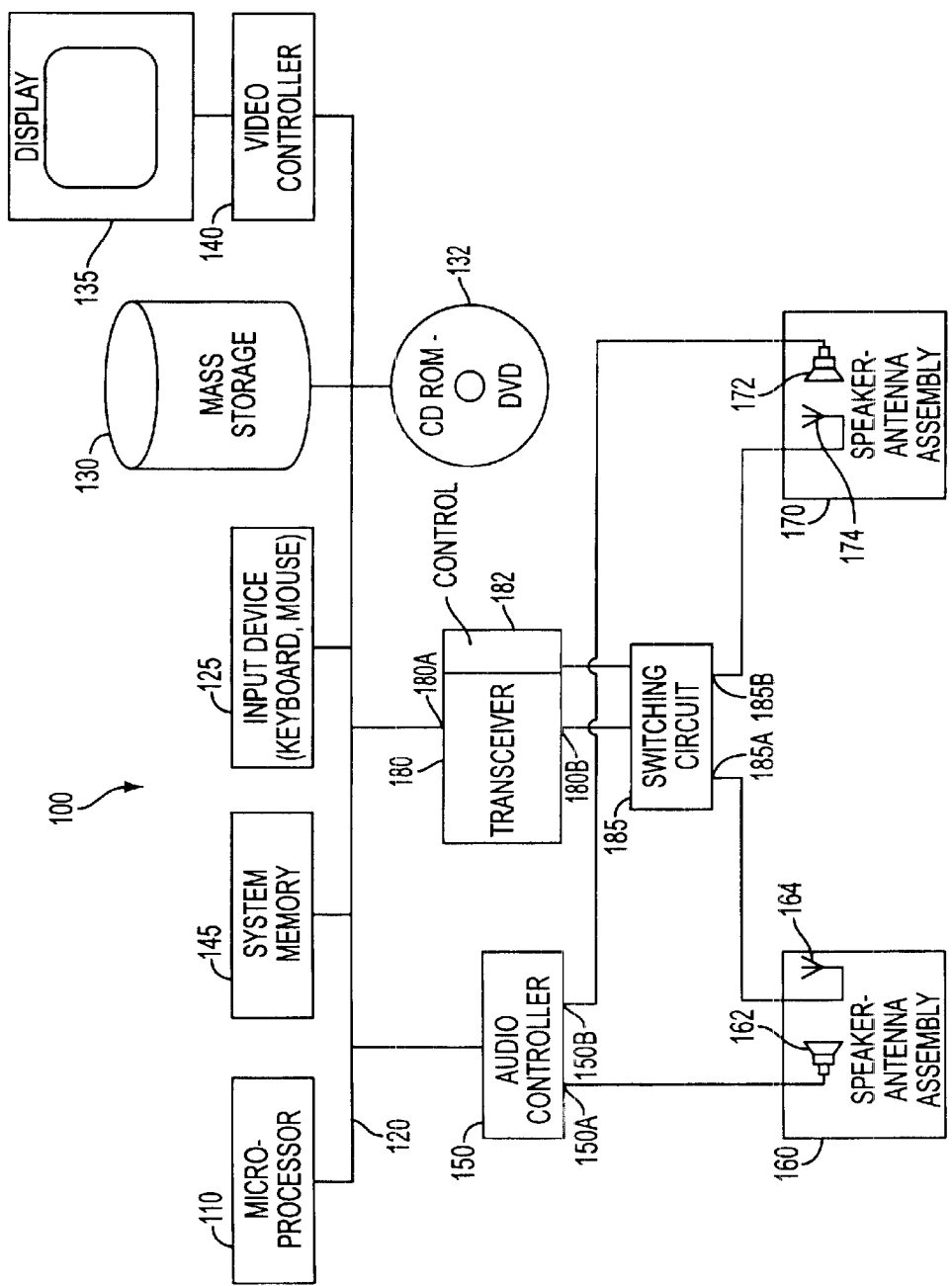
FIG. 1 is a block diagram depicting an embodiment of a computer system including speaker-antenna assemblies.

In one embodiment shown in FIG. 1, computer system 100 includes a microprocessor 110, for example a Pentium series microprocessor manufactured by Intel Corporation. Microprocessor 110 is coupled to a bus 120. Bus 120 servers as a connection between microprocessor 110 and other components of computer system 100. An input device 125 is coupled to microprocessor 110 to provide input to microprocessor 110. Examples of input devices include keyboards, touch screens, and pointing devices such as mouses, trackballs and track pads. Programs and data are stored in a mass storage device 130 which is coupled to microprocessor 110 via bus 120. Mass storage device 130 includes such devices as hard disks, optical disks, magneto-optical disks, floppy drives, CD-ROMs, DVDs and the like. A CD-ROM/DVD drive 132 is shown coupled to bus 120 as a representative example of mass storage. Computer system 100 further includes a display 135 which is coupled to microprocessor 110 by a video graphics controller 140. A system memory 145 is coupled to microprocessor 110 to provide the microprocessor with fast storage to facilitate execution of computer programs. It should be understood that other busses and intermediate circuits can be deployed between the components described above and microprocessor 110 to facilitate interconnection between the components and the microprocessor. Bridge chips (not shown) are used to couple the microprocessor to various conventional buses such as the PCI (Peripheral Component Interconnect) bus and the ISA (Industry Standard Architecture) bus to facilitate connection to interface cards and peripherals.

An audio controller 150 is coupled to bus 120 to provide right and left channel sound at audio outputs 150A and 150B, respectively. One example of an audio controller that can be employed as controller 150 is the Maestro 3i manufactured by ESS Technology, Inc.

Computer system 100 includes speaker-antenna assemblies 160 and 170. Speaker-antenna assembly 160 includes an audio speaker 162 and an antenna 164 which are both situated in a common support (shown later in FIG. 3 as support 300). Speaker-antenna assembly 170 includes an audio speaker 172 and an antenna 174 which are both situated in another common support (shown later in FIG. 3 as support 300).

A radio transceiver 180 includes an information port 180A and an RF port 180B. Information port 180A is coupled to bus 120 as shown. RE port 180B is coupled to switching circuit 185 which includes ports 185A and 185B that are coupled to antennas 164 and 174, respectively. Switching circuit 185 permits either antenna 164 or antenna 174 to be connected to transceiver 180 under the control of controller 182. More particularly, when the DC bias of switching circuit 185 is set to ON by controller 182, main antenna 174 is active and connected to the transceiver. However, when that DC bias is set to OFF, auxiliary antenna 164 is connected to the transceiver. Controller 182 facilitates determination of which antenna should be connected to the transceiver, as discussed later in more detail. One transceiver that may be employed as transceiver 180 is the ORiNOCO mini-PCI transceiver manufactured by Lucent Technologies.

Figure 2:
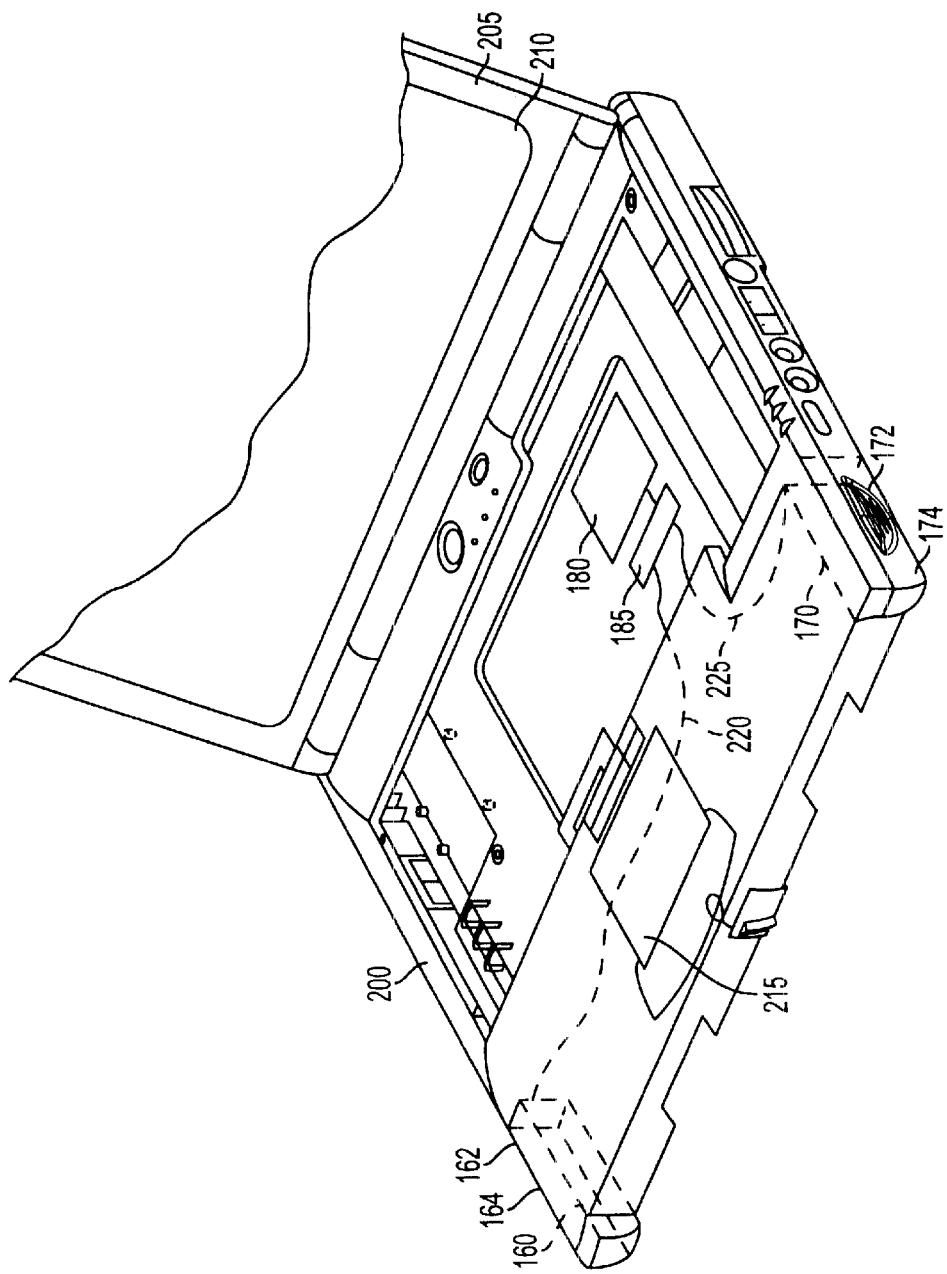
FIG. 2 is a perspective view of an embodiment of the computer system of FIG. 1.

FIG. 2 is a perspective view of computer system 100 including a base 200 and a display 205. In this particular example, display 205 includes a liquid crystal display (LCD) panel 210. Display 205 pivots with respect to base 200 to the open position shown in FIG. 2 and to a closed position, not shown. A touch pad input device 215 is provided at base 200 to permit the user to control cursor movement on the display. The keyboard situated between touch pad 215 and display 205 has been removed for easier viewing of relevant structures inside base 200. For example, transceiver 180 and switching circuit 185 are situated inside base 200 as shown. Speaker-antenna assemblies 160 and 170 are shown in dashed lines so that their locations in base 200 can be readily seen. Dashed lines are also used for coaxial cable lines 220 and 225 which connect the switched ports of switching circuit 185 to antennas 164 and 174, respectively. Audio cables (not shown) are used to connect audio controller 150 of FIG. 1 to speakers 162 and 172.

Figure 3:
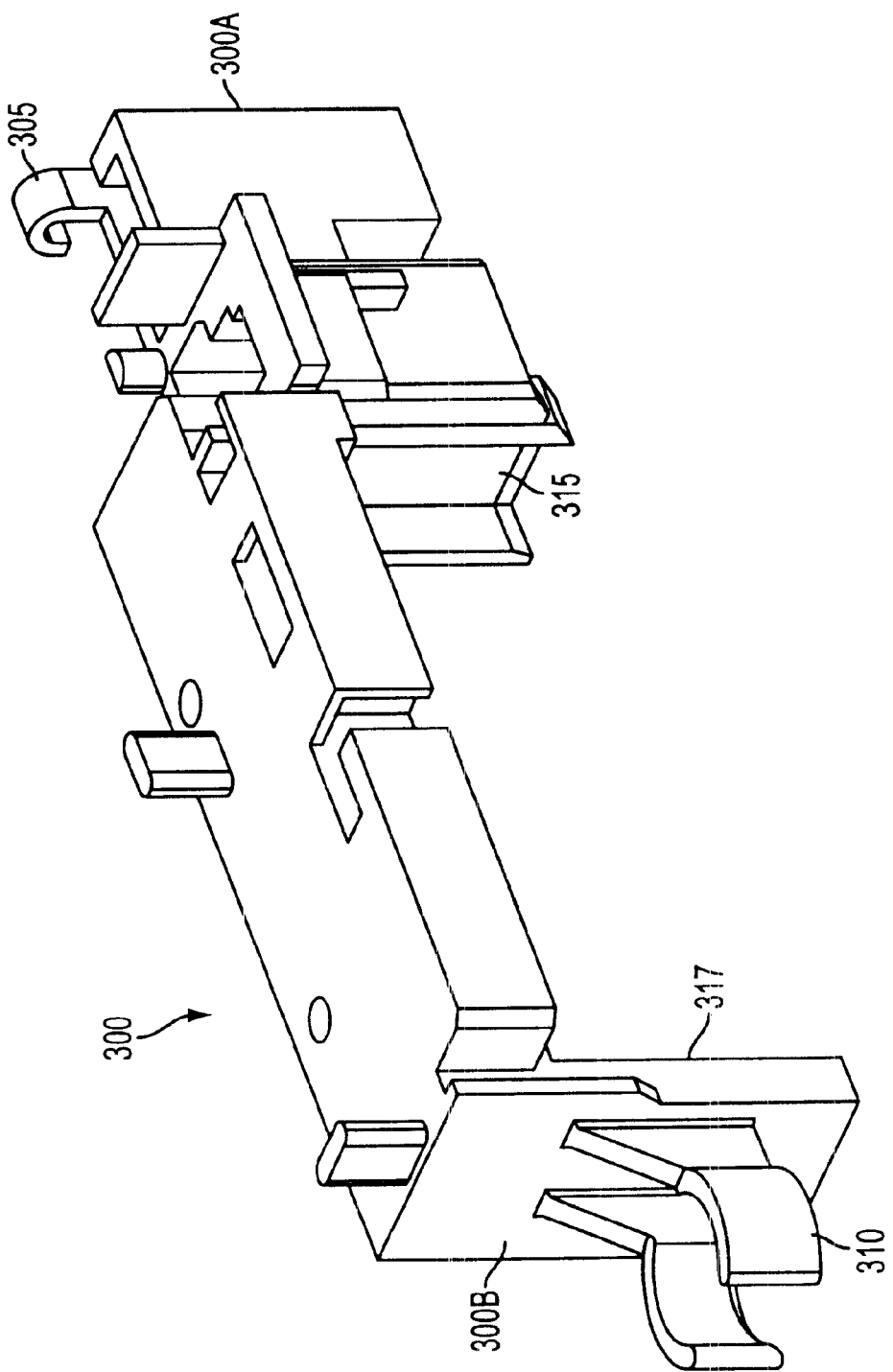
FIG. 3 is a perspective view illustrating an embodiment of the common support member of a speaker-antenna assembly.
Figure 4:
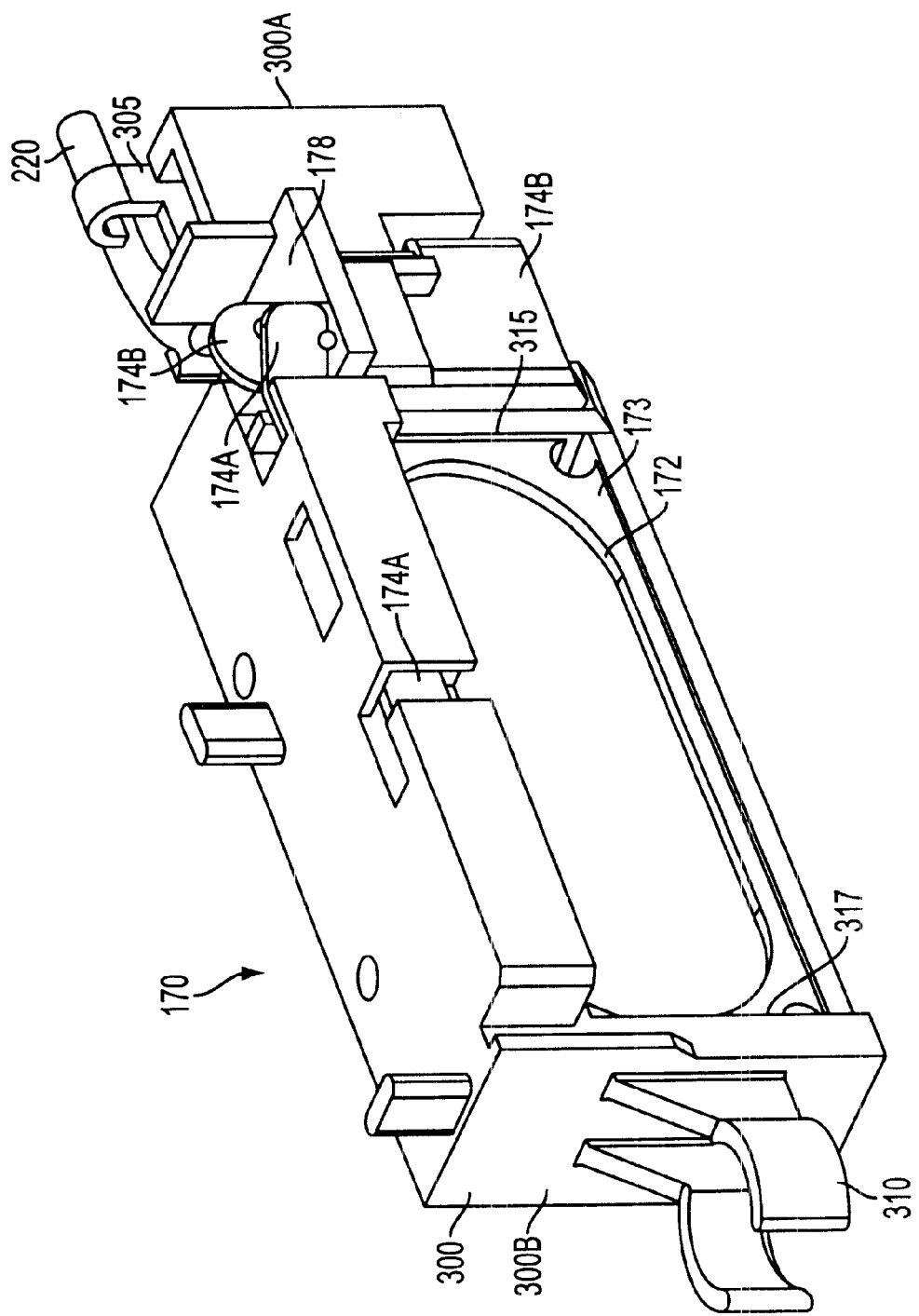
FIG. 4 is a perspective view of the speaker-antenna assembly of FIG. 1 showing the speaker and antenna located therein.

FIG. 3 is a perspective view of a support member 300 which together with speaker 172 and antenna 174 form speaker-antenna assembly 170 (FIG. 4). Support member 300 provides support and positioning to speaker 172 and antenna 174. Support member 300 includes a coaxial cable guide 305 at one end 300A and a positioning guide 310 at the opposite end 300B. Moreover, support member 300 includes opposed interior grooves 315 and 317 which slidably receive a speaker 172 therebetween as shown in FIG. 4.

FIG. 4 depicts the completed speaker-antenna assembly 170 with speaker 172 and antenna 174 installed therein. In this embodiment, antenna 174 is a dipole antenna including elements 174A and 174B connected at a feed point 178 to the center conductor and shield, respectively, of coaxial cable 220.

In one embodiment, speaker 172 includes a substantially rectangular housing 173 which slides between substantially symmetric opposed grooves 315 and 317. Support member 300 is molded from an electrically insulative material such as polyurethane.

Figure 5:
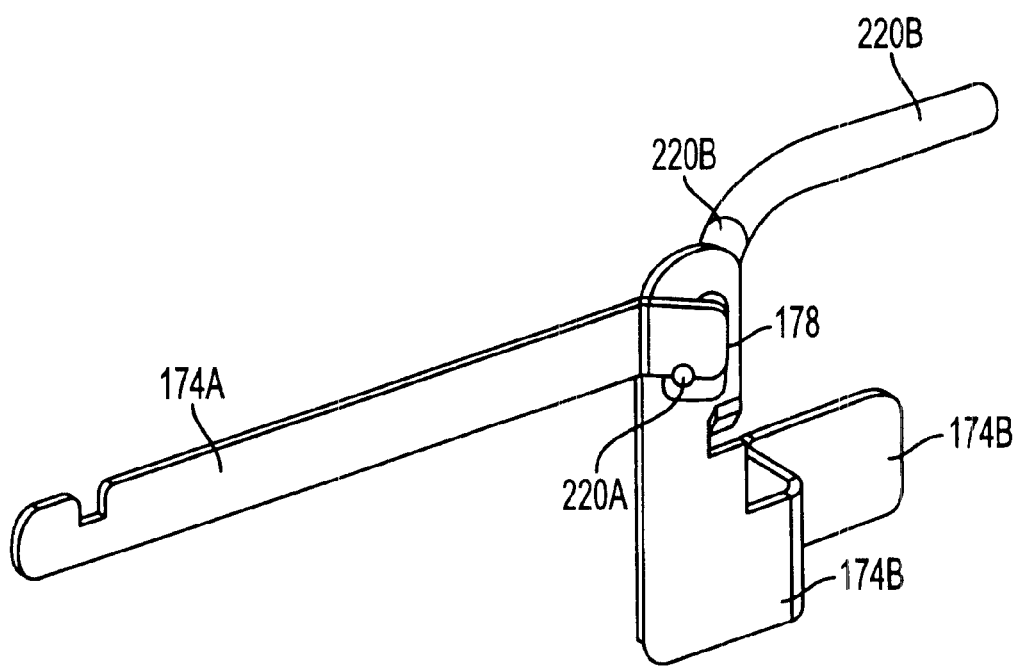
FIG. 5 is a perspective view illustrating an embodiment of the antenna elements and coaxial cable employed in the speaker-antenna assembly.

FIG. 5 is a perspective view of antenna elements 174A, 174B and coaxial cable 220 employed in the speaker-antenna assembly. Although partially hidden from view, coaxial cable 220 includes a center conductor 220A which is electrically coupled to antenna element 174A as shown. Coaxial cable 220 also includes a shield 220B which is electrically coupled to antenna element 174B.

Figure 6:
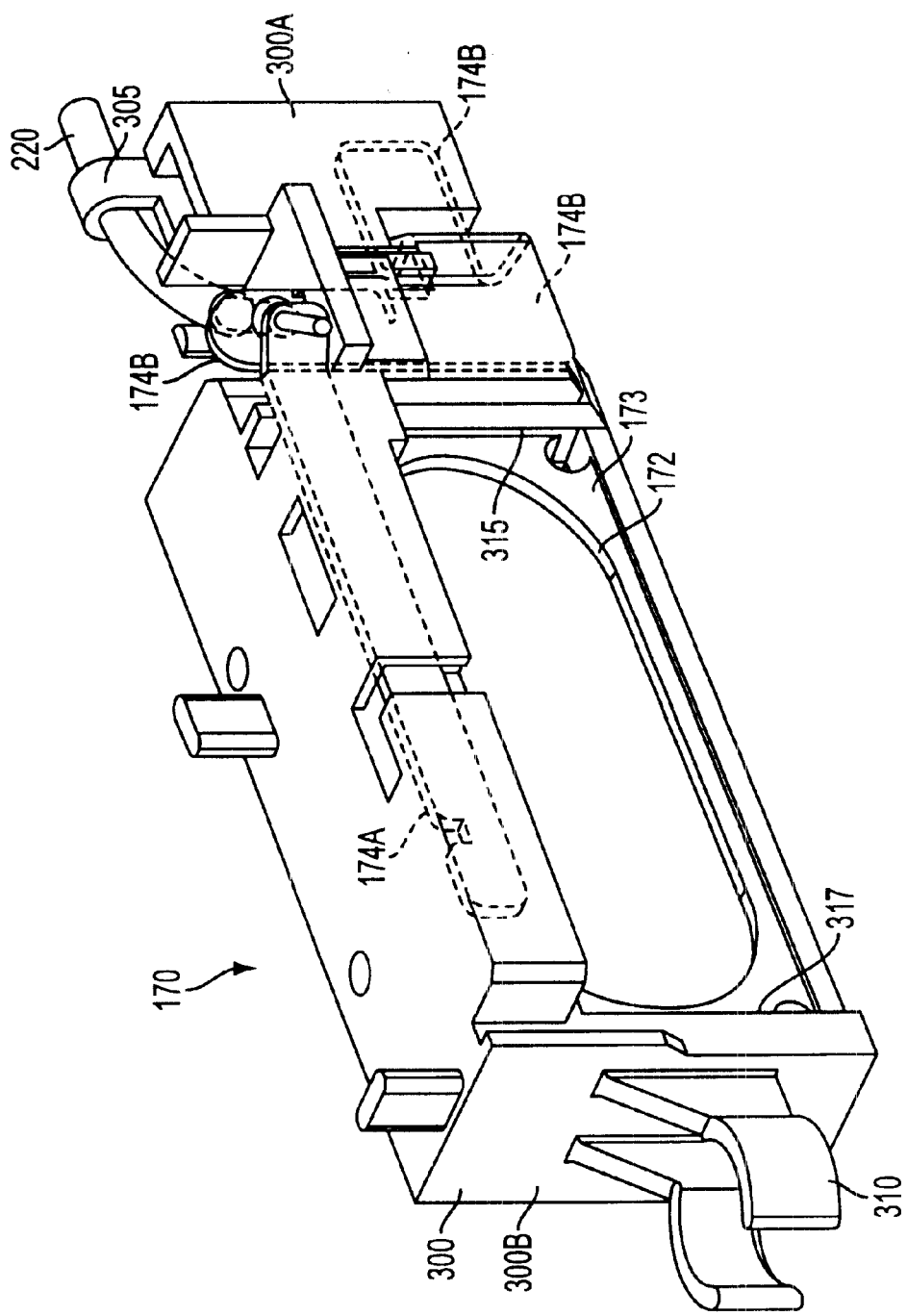
FIG. 6 is a close-up perspective view of a speaker-antenna assembly of FIG. 4 with hidden portions of the antenna elements being shown in dashed lines for added clarity.

FIG. 6 is a close-up perspective view of speaker-antenna assembly 170 with hidden portions of the antenna elements 174A and 174B being shown in dashed lines for added clarity.

Figure 7:
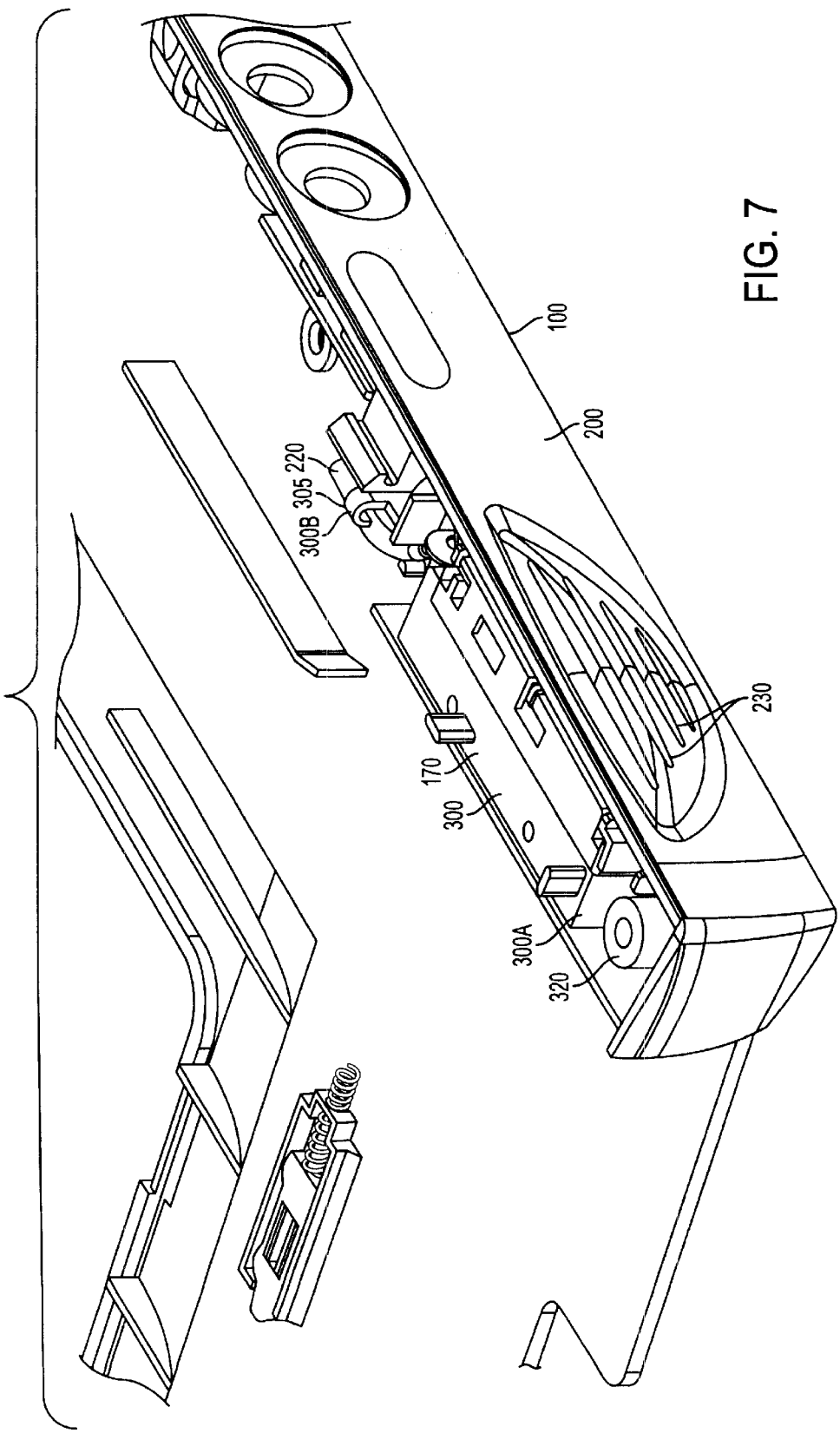
FIG. 7 is a perspective view illustrating an embodiment of a speaker-antenna assembly in the base of the computer system.

FIG. 7 is a perspective view of speaker-antenna assembly 170 mounted in operating position in base 200 of computer system 100. For clarity, portions of the computer system other than those adjacent speaker-antenna assembly 170 are not shown. Base 200 includes one or more apertures 230 adjacent speaker-antenna assembly 170 to permit sound to pass therethrough. For example, louvers can be employed as apertures 230 as shown. Base 200 includes a guide post 320 over which position guide 310 (not shown, see FIG. 4) slides to position and holds support member 300 to base 200.

Figure 8:
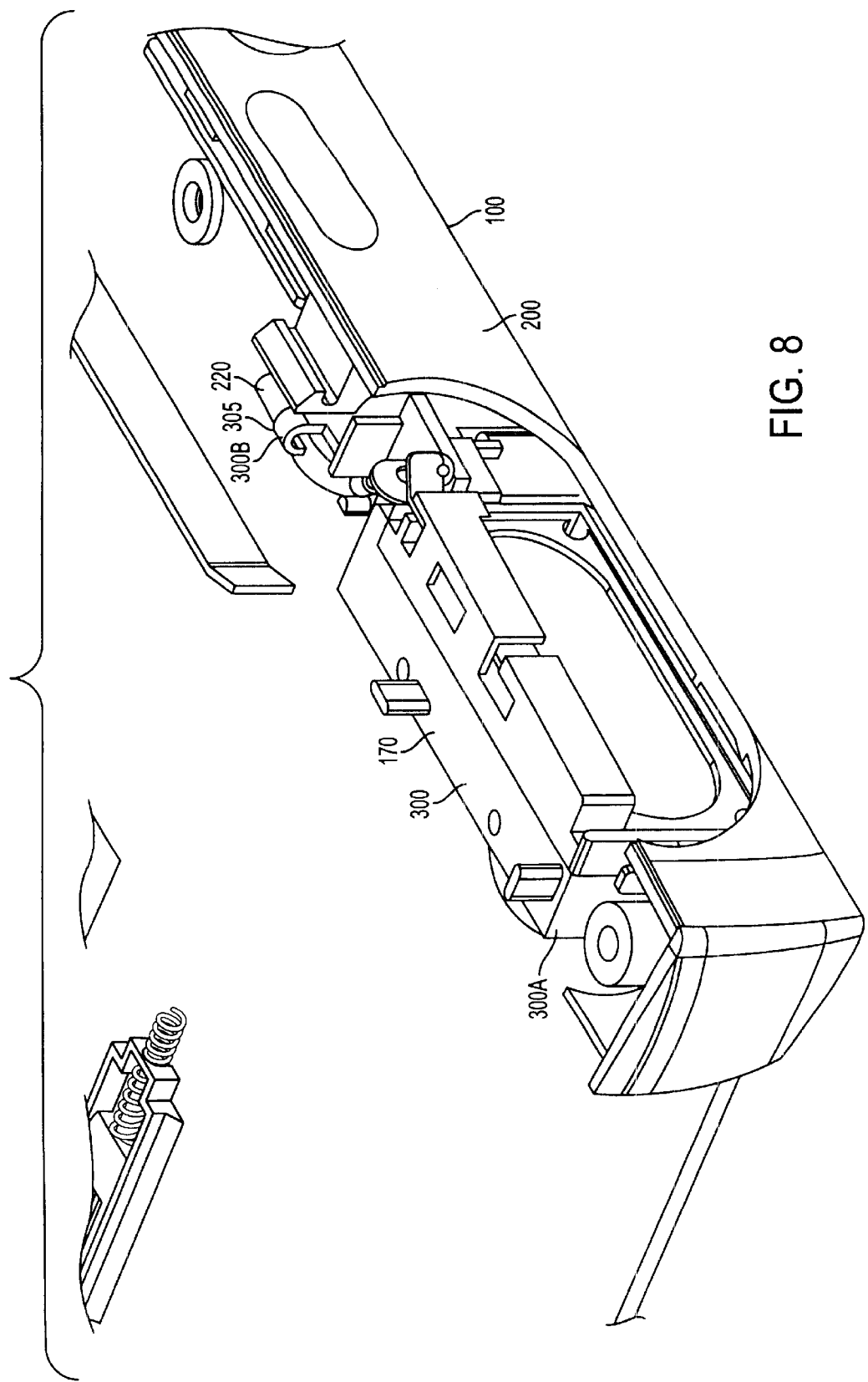
FIG. 8 is a perspective view similar to FIG. 7 except that a portion of the base is cut away to more clearly show the speaker-antenna assembly.

FIG. 8 is similar to the perspective view of FIG. 6 except with the portion of base 200 adjacent speaker-antenna assemble 170 being cut away to more clearly show assembly 170. When speaker-antenna assembly 170 is situated in base 200, an enclosure or chamber is formed therebetween which enhances the acoustic properties exhibited by the speaker. Air space around a speaker is utilized to improve the speaker's frequency response by forming an enclosure in this manner.

While a representative speaker-antenna assembly 170 has been discussed above, this discussion also applies to speaker-antenna assembly 160 which is similarly situated in base 200 on the side of base 200 opposite speaker-antenna assembly 170. Speaker-antenna assemblies 160 and 170 are situated in base 200 in spaced-apart relationship near the perimeter of base 200. This achieves two goals, namely providing stereo separation between the two speakers or other multi-speaker effect, and providing spatial separation between the antennas for space diversity operation. Transceiver 180 can be configured for space diversity operation wherein the transceiver selects the best signal either from antenna 164 or antenna 174. Switching circuit 185 switches between antenna 164 and antenna 174 over time to permit received signals to be sampled and tested to determine which is better. In this manner, the antenna with the better signal can be selected by the system. Received signal amplitude is one measure of signal superiority which can be used to select the better signal and antenna. Quieting is another measure of signal superiority.

Alternatively, frequency diversity operation is also possible. For example, transceiver 180 can be configured to select an operating frequency within the IEEE 802.11 frequency band (typically 2.42–2.4835 GHz) for antenna 164 and to select another frequency within the Bluetooth frequency band (also typically 2.42–2.4835 GHz) for antenna 174. In this scenario, each antenna is operating at a different frequency. When operating in this frequency range, spatial separation between antennas 164 and 174 of approximately 2.5 times the wavelength or more produces acceptable results. Approximately 20 dB or more of isolation between the two antennas is desirable. The distance between antennas 164 and 174 is selected to be sufficient to provide substantial isolation between the antennas in one embodiment. Alternatively, antennas 164 and 174 can be resized to enable these antennas and transceiver 180 to operate in different respective frequency bands.

In summary, antennas 164 and 174 can be similarly dimensioned to operate at substantially the same frequency or similar frequencies, or they can be dimensioned differently to operate at substantially different frequencies or different frequency bands.

Consistent with the teachings herein, an antenna can be situated in an electrically insulative speaker housing to form a fully integrated antenna/speaker assembly. Antenna performance or gain is enhanced by using the speaker's metal magnet as a reflector to direct the RF signal.

The principal advantage of these embodiments is the substantial saving of valuable computer real estate inside the computer system which is achieved by locating the speaker and antenna in a common assembly. Cable lengths are also advantageously reduced and cable reliability is increased. The radiation pattern of the speaker-antenna assemblies is not unduly distorted by locating the speaker-antenna assemblies as described and substantial RF noise is avoided.

Although illustrative embodiments have been shown and described, a wide range of modification, change and substitution is contemplated in the foregoing disclosure and in some instances, some features of an embodiment may be employed without a corresponding use of other features. Accordingly, it is appropriate that the appended claims be construed broadly and in a manner consistent with the scope of the embodiments disclosed herein.

What is claimed is:

1. A computer system comprising:
   a base including an input device;
   a processor situated in the base;
   a memory, coupled to the processor, to facilitate execution of computer programs by the processor;
   a display connected to the base; and
   a first speaker-antenna assembly positioned on a guide member in the base and including:
   a support member;
   a speaker mounted in the support member; and
   an antenna mounted in the support member.

2. The computer system of claim 1 wherein the antenna is inserted into the support member.

3. The computer system of claim 2 wherein the speaker is inserted into the support member.

4. The computer system of claim 1 wherein the antenna includes first and second antenna elements inserted into the support member.

5. The computer system of claim 4 wherein the antenna elements are interconnected by a cable.

6. A computer system comprising:
   a base including a input device;
   a processor situated in the base;
   a memory, coupled to the processor, to facilitate execution of computer programs by the processor;
   a display mounted to the base;
   first and second support members mounted on a guide member in the base;
   first and second speakers respectively mounted in the support members and situated in the computer system in spaced apart relationship; and
   first and second antennas respectively situated in the first and second support members.

7. The computer system of claim 6 further comprising a radio transceiver coupled to the first and second antennas.

8. The computer system of claim 7 further comprising a switching circuit coupled between the radio transceiver and the first and second antennas.

9. The computer system of claim 8 wherein the first and second antennas are dimensioned to operate at different frequencies, respectively.

10. The computer system of claim 9 wherein the transceiver is capable of operating at the different frequencies.

11. The computer system of claim 8 wherein the first and second antennas are dimensioned to operate at substantially the same frequency.

12. The computer system of claim 8 wherein the switching circuit switches between the first and second antennas to provide space diversity operation.

13. The computer system of claim 6 wherein the display is pivotally mounted to the base.

14. An information handling system comprising:
    a base including a input device;
    a processor situated in the base;
    a memory, coupled to the processor, to facilitate execution of computer programs by the processor;
    a display pivotally mounted to the base;
    first and second support members mounted in the base;
    first and second speakers respectively slidably inserted in the support members and situated in the base in spaced apart relationship; and
    first and second antennas respectively inserted in the first and second support members.

15. The system of claim 14 further comprising a radio transceiver coupled to the first and second antennas.

16. The system of claim 15 further comprising a switching circuit coupled between the radio transceiver and the first and second antennas.

17. The system of claim 16 wherein the first and second antennas are dimensioned to operate at different frequencies, respectively.

18. The system of claim 17 wherein the transceiver is capable of operating at the different frequencies.

19. The system of claim 16 wherein the first and second antennas are dimensioned to operate at substantially the same frequency.

20. The system of claim 16 wherein the switching circuit switches between the first and second antennas to provide space diversity operation.

* * * * *